United States Patent
Henderson

(10) Patent No.: US 12,121,446 B1
(45) Date of Patent: Oct. 22, 2024

(54) MODULAR IMPLANT FOR COMBINATION HIP REPLACEMENT WITH INTRAMEDULLARY ROD

(71) Applicant: Dartmouth-Hitchcock Clinic, Lebanon, NH (US)

(72) Inventor: Eric R. Henderson, Lebanon, NH (US)

(73) Assignee: Dartmouth-Hitchcock Clinic, Lebanon, NH (US)

(*) Notice: Subject to any disclaimer, the term of this patent is extended or adjusted under 35 U.S.C. 154(b) by 0 days.

(21) Appl. No.: 17/173,346

(22) Filed: Feb. 11, 2021

Related U.S. Application Data

(60) Provisional application No. 62/972,728, filed on Feb. 11, 2020.

(51) Int. Cl.
*A61F 2/36* (2006.01)
*A61F 2/30* (2006.01)

(52) U.S. Cl.
CPC ............ *A61F 2/3609* (2013.01); *A61F 2/367* (2013.01); *A61F 2/3676* (2013.01); *A61F 2002/30345* (2013.01); *A61F 2002/30606* (2013.01); *A61F 2002/30649* (2013.01); *A61F 2002/3611* (2013.01); *A61F 2002/3647* (2013.01); *A61F 2002/3652* (2013.01)

(58) Field of Classification Search
CPC .. A61F 2002/30339; A61F 2002/30345; A61F 2002/30336; A61F 2002/30331; A61F 2002/30357; A61F 2002/3652; A61F 2002/30614; A61F 2/4684; A61F 2002/30329; A61F 2002/30332; A61F 2002/30616; A61F 2/4607
See application file for complete search history.

(56) References Cited

U.S. PATENT DOCUMENTS

| | | | | |
|---|---|---|---|---|
| 5,658,349 A * | 8/1997 | Brooks | ................ | A61F 2/3662 623/23.23 |
| 5,755,789 A * | 5/1998 | Deckner | ................ | A61F 2/3609 623/11.11 |
| 5,935,169 A * | 8/1999 | Chan | .................... | A61F 2/0095 606/62 |
| 6,264,699 B1 * | 7/2001 | Noiles | ................... | A61F 2/3859 623/22.41 |
| 6,319,286 B1 * | 11/2001 | Fernandez | ............ | A61F 2/3609 623/23.18 |
| 6,322,591 B1 * | 11/2001 | Ahrens | .................. | A61B 17/72 606/62 |
| 6,355,068 B1 * | 3/2002 | Doubler | .................... | A61F 2/36 623/23.18 |

(Continued)

*Primary Examiner* — Alvin J Stewart
(74) *Attorney, Agent, or Firm* — Loginov & Associates, PLLC; William A. Loginov

(57) ABSTRACT

This invention provides a device and treatment method for replacing the hip (in either a hemiarthroplasty or total hip arthroplasty), which protects the remainder of the femur from fracture. Such a device is highly applicable to the treatment of patients with current or impending fractures of the femur, particularly those with metastatic bone cancer, where there is concern for current or future metastatic disease of the femoral neck or head, which would necessitate hip replacement. The implant consists of a two-piece arrangement with a separate femoral component and a securing, intermedullary rod/nail that is received in a locking arrangement by a longitudinal fenestration of the femoral component.

14 Claims, 5 Drawing Sheets

(56) References Cited

U.S. PATENT DOCUMENTS

| | | | |
|---|---|---|---|
| 6,524,342 B1* | 2/2003 | Muhlhausler | A61F 2/4059 623/22.45 |
| 6,905,515 B1* | 6/2005 | Gilbertson | A61F 2/367 623/23.46 |
| 7,766,968 B2* | 8/2010 | Sweeney | A61F 2/4607 623/19.11 |
| 8,029,573 B2* | 10/2011 | Podolsky | A61B 17/1668 623/22.42 |
| 8,623,093 B2* | 1/2014 | Dickerson | A61F 2/30734 623/22.4 |
| 9,237,949 B2* | 1/2016 | Podolsky | A61B 17/164 |
| 9,427,322 B1* | 8/2016 | Serafin, Jr. | A61F 2/3662 |
| 2002/0038148 A1* | 3/2002 | Fernandez | A61F 2/30734 623/23.18 |
| 2002/0040244 A1* | 4/2002 | Despres, III | A61F 2/36 623/23.23 |
| 2002/0042655 A1* | 4/2002 | Hayes, Jr. | A61F 2/367 623/23.22 |
| 2002/0058999 A1* | 5/2002 | Dwyer | A61F 2/36 623/23.18 |
| 2002/0111692 A1* | 8/2002 | Ralph | A61F 2/30734 623/23.23 |
| 2003/0074078 A1* | 4/2003 | Doubler | A61F 2/36 623/23.18 |
| 2003/0149486 A1* | 8/2003 | Huebner | A61F 2/4657 623/908 |
| 2003/0149487 A1* | 8/2003 | Doubler | A61B 17/8869 623/22.42 |
| 2003/0204268 A1* | 10/2003 | Gerbec | A61F 2/4637 623/20.15 |
| 2003/0204269 A1* | 10/2003 | Gerbec | A61F 2/30734 623/20.15 |
| 2004/0019386 A1* | 1/2004 | Ferree | A61F 2/442 623/23.22 |
| 2004/0064186 A1* | 4/2004 | McCleary | A61B 17/1659 623/18.11 |
| 2004/0117024 A1* | 6/2004 | Gerbec | A61F 2/38 623/20.15 |
| 2004/0122440 A1* | 6/2004 | Daniels | A61F 2/4657 606/102 |
| 2004/0122525 A1* | 6/2004 | Daniels | A61F 2/4684 623/22.42 |
| 2005/0090904 A1* | 4/2005 | Howie | A61F 2/30721 623/23.26 |
| 2005/0125067 A1* | 6/2005 | Sweeney | A61F 2/4612 623/23.46 |
| 2005/0143828 A1* | 6/2005 | Collins | A61F 2/36 623/18.11 |
| 2005/0288794 A1* | 12/2005 | Khalili | A61F 2/30721 623/22.41 |
| 2006/0052877 A9* | 3/2006 | Doubler | A61F 2/36 623/23.18 |
| 2007/0005146 A1* | 1/2007 | Heyligers | A61F 2/367 623/22.41 |
| 2007/0043447 A1* | 2/2007 | Cheal | A61F 2/3662 623/22.46 |
| 2008/0125867 A1* | 5/2008 | McCleary | A61F 2/4684 623/23.11 |
| 2008/0161811 A1* | 7/2008 | Daniels | A61B 17/1739 606/80 |
| 2008/0281430 A1* | 11/2008 | Kelman | A61F 2/30767 623/23.23 |
| 2010/0094292 A1* | 4/2010 | Parrott | A61B 17/7241 606/62 |
| 2012/0010720 A1* | 1/2012 | Dickerson | A61F 2/3607 623/22.42 |
| 2019/0254782 A1* | 8/2019 | Branemark | A61C 8/0066 |
| 2020/0323575 A1* | 10/2020 | Cortes Cubero | A61F 2/4014 |
| 2022/0039959 A9* | 2/2022 | Somani | A61F 2/3662 |

* cited by examiner

MODULAR IMPLANT FOR COMBINATION HIP REPLACEMENT WITH INTRAMEDULLARY ROD

RELATED APPLICATION

This application claims the benefit of U.S. Provisional Application Ser. No. 62/972,728, entitled MODULAR IMPLANT FOR COMBINATION HIP REPLACEMENT WITH INTRAMEDULLARY ROD, filed Feb. 11, 2020, the teachings of which are expressly incorporated herein by reference.

FIELD OF THE INVENTION

This invention relates to implantable orthopedic devices for the hip, and more generally to devices for use in hip replacements.

BACKGROUND OF THE INVENTION

Hip replacement (arthroplasty) is a surgical procedure in which the hip joint is replaced by a prosthetic implant, also known as a hip prosthesis or implant. Hip replacement surgery can be performed as a total replacement or a hemi (half) replacement (hemiarthroplasty). Such joint replacement orthopedic surgery is generally conducted to relieve arthritis pain, treat some hip fractures, or to address numerous other conditions including cancer. A total hip replacement (total hip arthroplasty or THA) consists of replacing both the acetabulum and the femoral head while hemiarthroplasty generally only replaces the femoral head. Hip replacement is currently one of the most common orthopedic operations.

In the setting of patients with metastatic cancer involving the femur, surgery is often performed to prevent or treat a fracture of the femur. In this setting, one of two types of implants are usually selected. In the setting of a metastatic lesion affecting the femoral head, an arthroplasty implant is usually selected. In the setting of a metastatic lesion affecting the femoral shaft, an intramedullary rod (or nail) is usually selected. Selection of an implant is made more difficult in the setting of a femur affected with a lesion of the femoral head and a concomitant lesion of the femoral shaft. Furthermore, placement of an arthroplasty implant prevents the placement of an intramedullary implant and vice versa. This is unfortunate because it is desirable to protect the entire shaft of the femur in the setting of metastatic cancer, however, arthroplasty implants are not capable of spanning the entire femur and similarly intramedullary implants, which are capable of spanning the entire femur, are incapable of replacing the femoral head.

More particularly, in the case of protection from fracture of the femoral shaft and intertrochanteric region, cephalomedullary nail (a.k.a. rod) implants are typically employed. For avoidance/treatment of fracture of the femoral neck or head a partial or total hip replacement is typically performed.

It is desirable to provide a device, and associated system for implantation, which would be used to replace the hip (hemiarthroplasty or total hip arthroplasty) and protect the remainder of the femur from fracture. Such a device should have strong relevance in the treatment of patients with current or impending fractures of the femur, especially those with metastatic bone cancer, where there is concern for current or future metastatic disease of the femoral neck or head, which would necessitate hip replacement.

SUMMARY OF THE INVENTION

This invention overcomes disadvantages of the prior art by providing a device used to replace the hip (in either a hemiarthroplasty or total hip arthroplasty) and protect the remainder of the femur from fracture. Such a device is highly applicable to the treatment of patients with current or impending fractures of the femur, particularly those with metastatic bone cancer, where there is concern for current or future metastatic disease of the femoral neck or head, which would necessitate hip replacement. The implant consists of a two-piece arrangement. separate femoral component and a securing, intramedullary rod/nail that is received in a locking arrangement by a longitudinal fenestration of the femoral component.

In an illustrative embodiment, an implant for use in hip replacement is provided, and includes a femoral component, in conjunction with a securing, intramedullary rod that is received in a locking arrangement by a longitudinal fenestration of the femoral component. Illustratively, the femoral component and the rod engage at a tapered interconnection. The femoral component can define a shaft adapted the seat within a cavity formed in a proximal end of a patient's femur. The rod can include at least one securing fastener at a distal end thereof. The femoral component can include an arm that carries a ball joint. At least one of the femoral component and the rod can be arranged to be cemented into the cavity.

In a further illustrative embodiment, a for hip replacement method is provided. It includes the step of (a) preparing a proximal end of a patients femur to define a cavity for receiving an implant having a ball joint; (b) inserting, into the cavity, a first component of the implant; and (c) inserting a second component into the cavity in engagement with the first component proximate to the proximal end. Illustratively, the first component is a femoral component having the ball joint and a shaft with a fenestration, and the second component is an intramedullary rod that engages the fenestration in a locking relationship. The fenestration and a proximal end of the rod can each define engaging tapered segments that are sized and arranged to interengage in the locking relationship. The first component can be an intramedullary rod, and the second component can be a femoral component having the ball joint and a shaft with a fenestration, wherein a proximal end of the rod engages the fenestration. Either the first component or the second component can be an intramedullary rod. In this case, the intramedullary rod can be secured into the cavity with at least one of fastener(s) and cement.

BRIEF DESCRIPTION OF THE DRAWINGS

The invention description below refers to the accompanying drawings, of which.

DETAILED DESCRIPTION

I. Prior Implementations

Figure 1:
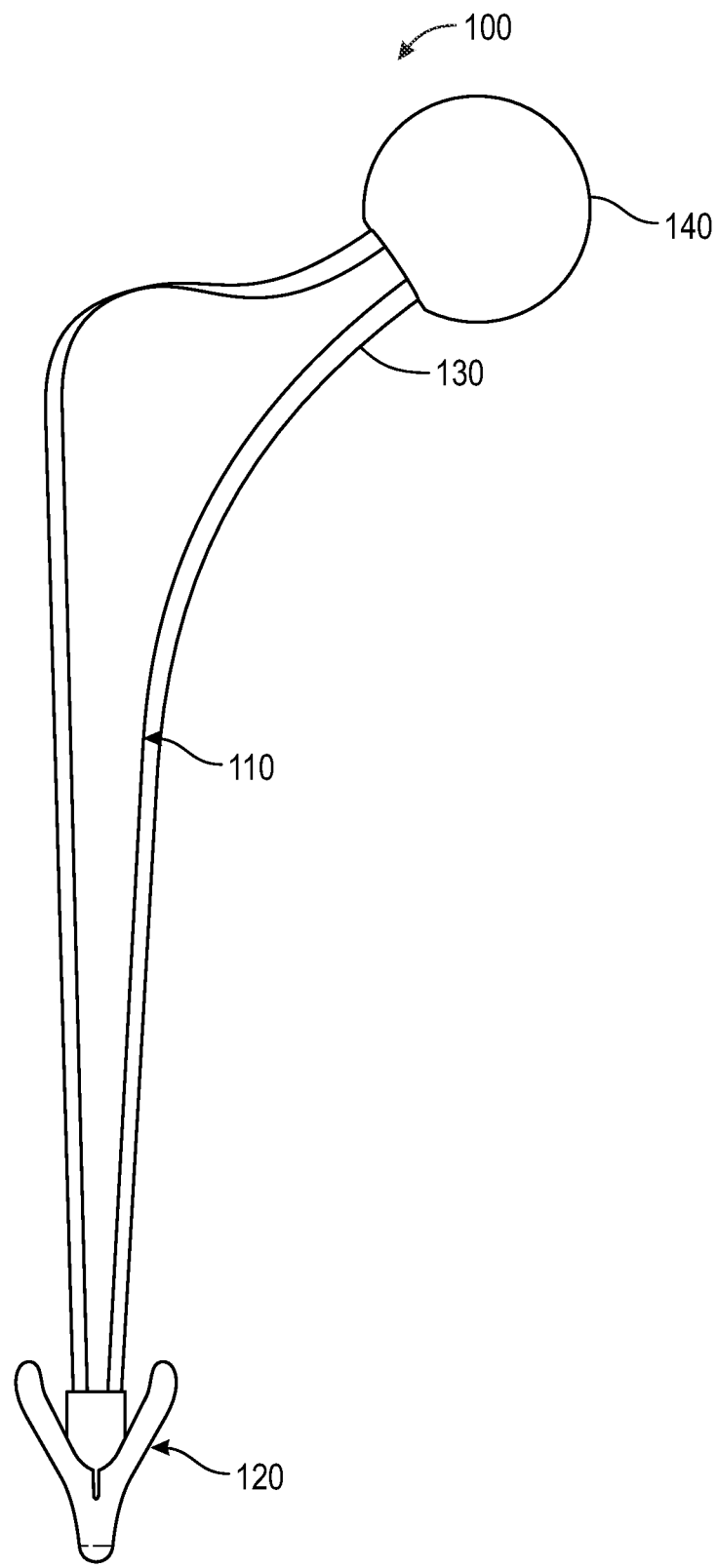
FIG. 1 is a side view of a conventional cemented femoral component for use in hip replacement procedures according to a prior art implementation in which the component defines a one-piece construction.

FIG. 1 shows a conventional (cemented) femoral implant component 100 according to a prior art implementation. As described above, this component 100 consists of a single, unitary construction that can be manufactured using various metal-forming techniques, or combination of such techniques. The component 100 consists of a shaft 110 adapted to seat within a cavity formed in the patient's femur, and includes an expanding, distal anchor 120. The shaft 110 is adapted to be cemented in place for a permanent affixation. The proximal end of the shaft 110 carries a transverse arm 130 with a ball 140 at its end. The ball 140 rotatably engages a cup that is affixed to the hip bone. The component 100 is provided in various sizes and configurations, which are collectively suited to accommodate the skeletal structures of the vast majority of patients.

Figure 2:
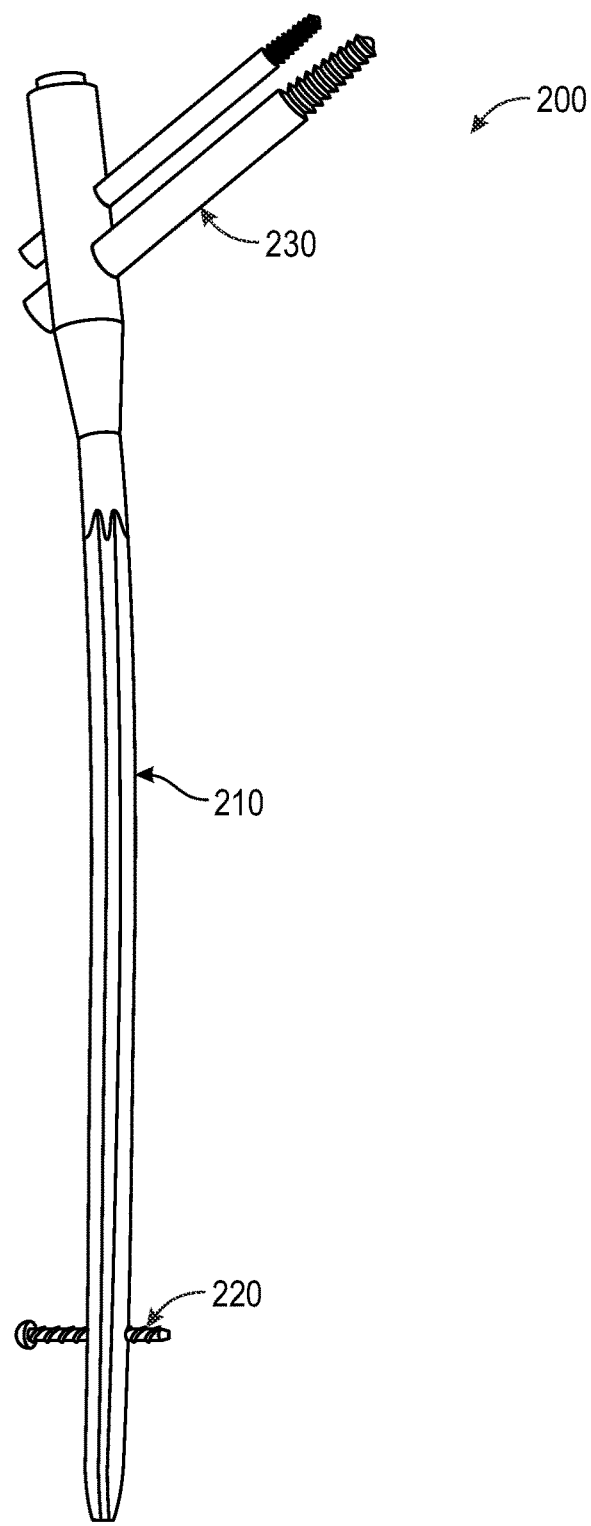
FIG. 2 is a side view of a conventional cephalomedullary nail for use in certain hip replacement procedures according to a prior art implementation.

According to another implementation, FIG. 2 shows a modular component 200 having a cephalomedullary nail 210 with a threaded proximal arm assembly 230 for securing a separate ball joint assembly (not shown). The distal end of the shaft 210 includes a through hole for securing a conventional holding screw 220. This screw 220 is inserted through a transverse hole formed in the femur after the nail 210 is fully inserted into a cavity formed therein. The screw 220 threads through a hole in the nail 210, and is thereby used to affix the shaft in place against longitudinal (also termed "axial") motion (push-in or pull-out).

However, as described above, these components 100, 200 may be unsuitable to patients suffering from degenerative bone conditions, such as certain forms of bone cancer, in which fractures may weaken the ability of the femur to retain the rod/nail 110 or require replacement after initial implantation.

II. Modular Implant

Figure 3:
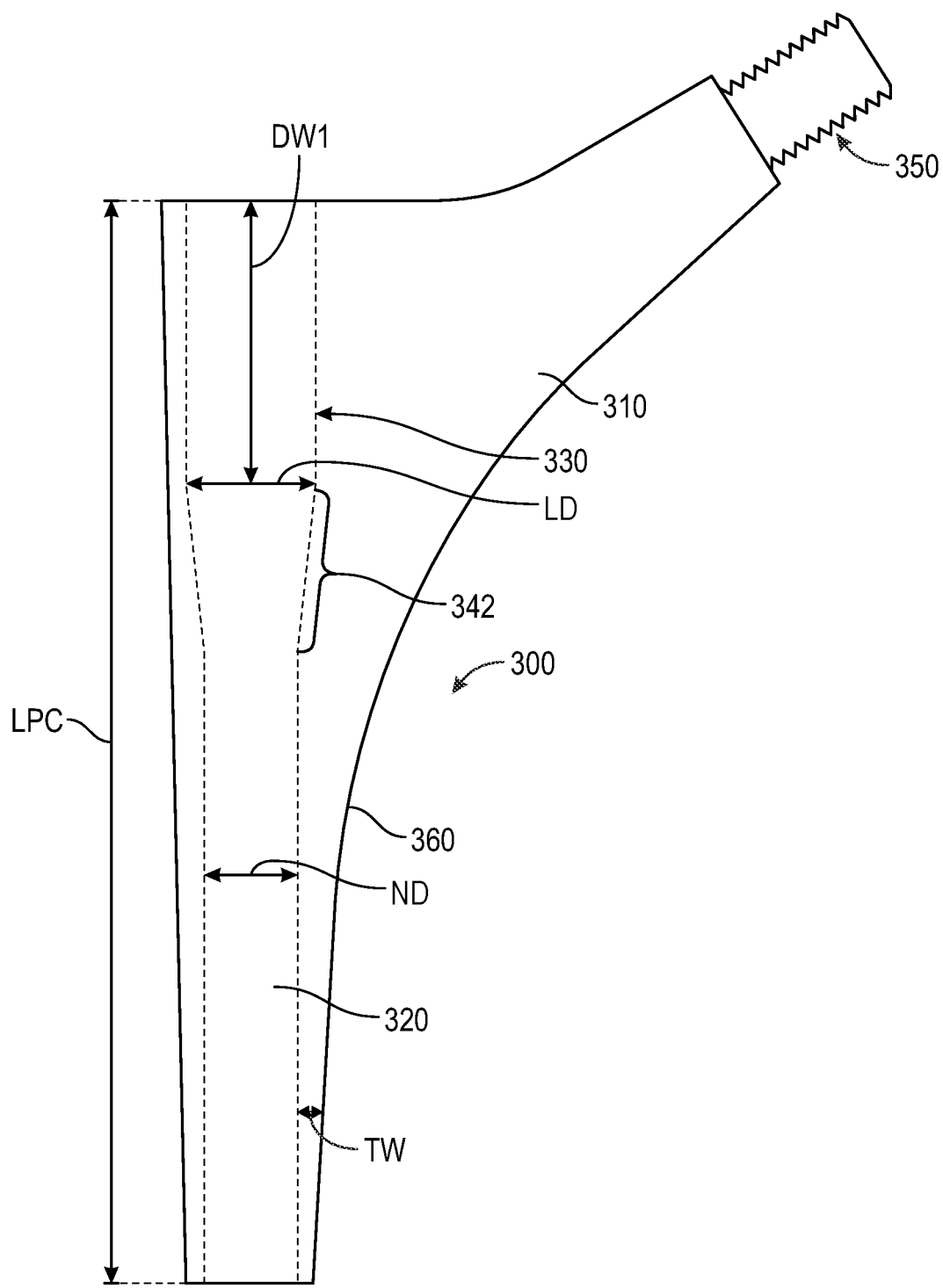
FIG. 3 is an partial exposed side view of a femoral with a longitudinal fenestration to allow passage of intramedullary rod/nail locking into femoral component according to an illustrative embodiment.
Figure 4:
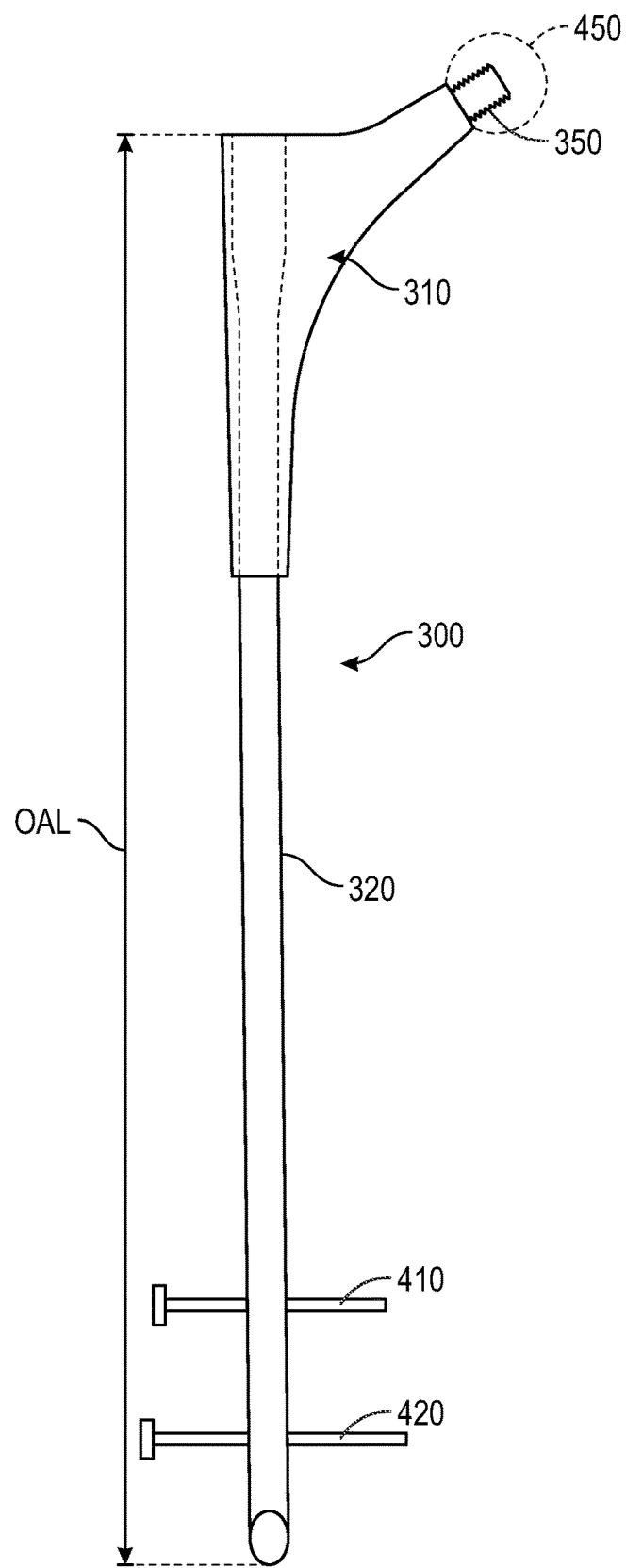
FIG. 4 is a exposed side view of an intramedullary rod/nail locked into the femoral component, generally according to FIG. 3, with (e.g.) two distal interlocking screws provided thereto at the distal end thereof.

Reference is made to FIGS. 3 and 4, which show a modular femoral implant 300 for hip replacement procedures according to an illustrative embodiment. The component(s) of the implant 300 can be constructed from any acceptable biocompatible material, or a combination of materials—for example, stainless steel and/or titanium alloy. Such construction techniques and materials should be clear to those of skill.

The depicted implant 300 has been modified to allow a proximal (femoral) component 310 to be rigidly connected with an intramedullary implant ("nail" or "rod") 320 similar in geometry to conventional intermedullary nail 200 shown in FIG. 2. The structure is sized and angled similarly to a conventional implant as described above—in general, it can be constructed in one or more sizes/angles depending upon the physiology of the implant recipient. The implant 300 therefore defines an overall length OAL that is of a conventional size range. As shown in FIG. 4, the distal end of the intermedullary rod component 320 includes at least one (two are depicted) retaining screws 410 and 420 to secure the rod within the femur cavity (described further below). As shown in FIG. 3, an inner well or fenestration 330 is formed longitudinally within the elongated length of the proximal component 310. This fenestration defines a larger diameter LD of approximately 12 millimeters at the proximal-most (cranial) end for a distance DW1 of approximately 20-30 millimeters. The fenestration/well 330 tapers, distally along a segment 342 of approximately 15-20 millimeters in length to a narrower diameter ND of approximately 9 millimeters, which thereafter remains substantially constant to the distal-most tip of the femoral component 310. The component defines a length LPC of approximately 160 mm. This length is variable in alternate implementations. The fenestration 330 is sized relative to the outer perimeter of the femoral component 310 so as to maintain a minimal wall thickness TW that is sufficient to avoid failure of the femoral component 310 under expected loads.

The proximal end of the rod 320 is shown inserted in the fenestration 330 of the femoral component 310 in a manner that defines a close engagement therebetween. That is, the outer surface/diameter(s) of the proximal end of the rod 320 are sized to closely conform to the shape of the inner geometry of the fenestration 330. The flared or tapered segment 342 allows for an effective locking fit between components that avoids play therebetween when sufficient axial holding force is applied. This interfering fitment is sometimes termed a "Morse taper."

Illustratively, the femoral component 310 defines an outer shape similar to the cemented implant 100 shown in FIG. 1. It can include a threaded end 350 adapted to receive an appropriately sized ball joint (see ball 450 (shown in phantom) in FIG. 4). The femoral component's elongated shaft 360 can be adapted to be inserted into the femur via a non-cemented (a.k.a. press-fit or scratch-fit) technology or a cemented technology both of which techniques should be clear to those of skill. In an exemplary embodiment, the elongated shaft 360 of the femoral component 310 can be implemented as a cemented implant. Once cemented in place, the intramedullary rod/nail portion 320 of the implant 300 is measured, and then driven into place using (e.g.) a medical grade mallet. The rod/nail can be cemented or non-cemented.

More particularly, the implant 300 is arranged to be assembled to engage together in either of two general orderings. In a first ordering, the femoral component 310 is placed into the femoral cavity first, followed by the addition of the rod/nail 320 through the fenestration 330 in the femoral component 310. The rod/nail 320 is thereafter locked in place via the Morse taper fit, cement and/or screw(s) 410, 420.

In a second, alternate ordering, the taper fit is omitted or reversed, and the intermedullary rod/nail is placed first into the femur cavity—where it is secured by cement, nails, etc. A similarly shaped femoral component (to that of FIGS. 3 and 4) is then slid over the proximal end of the inserted rod/nail so that the proximal end of the rod/nail engages an appropriately sized/tapered (conforming) well/fenestration formed longitudinally in the femoral component. Alternatively, the fenestration and (engaging) proximal end of the rod/nail can be threaded, or include another form of locking mechanism—e.g. set screws—to resist/avoid axial motion between the assembled implant components in this arrangement.

III. Method of Assembly and Attachment

Figure 5:
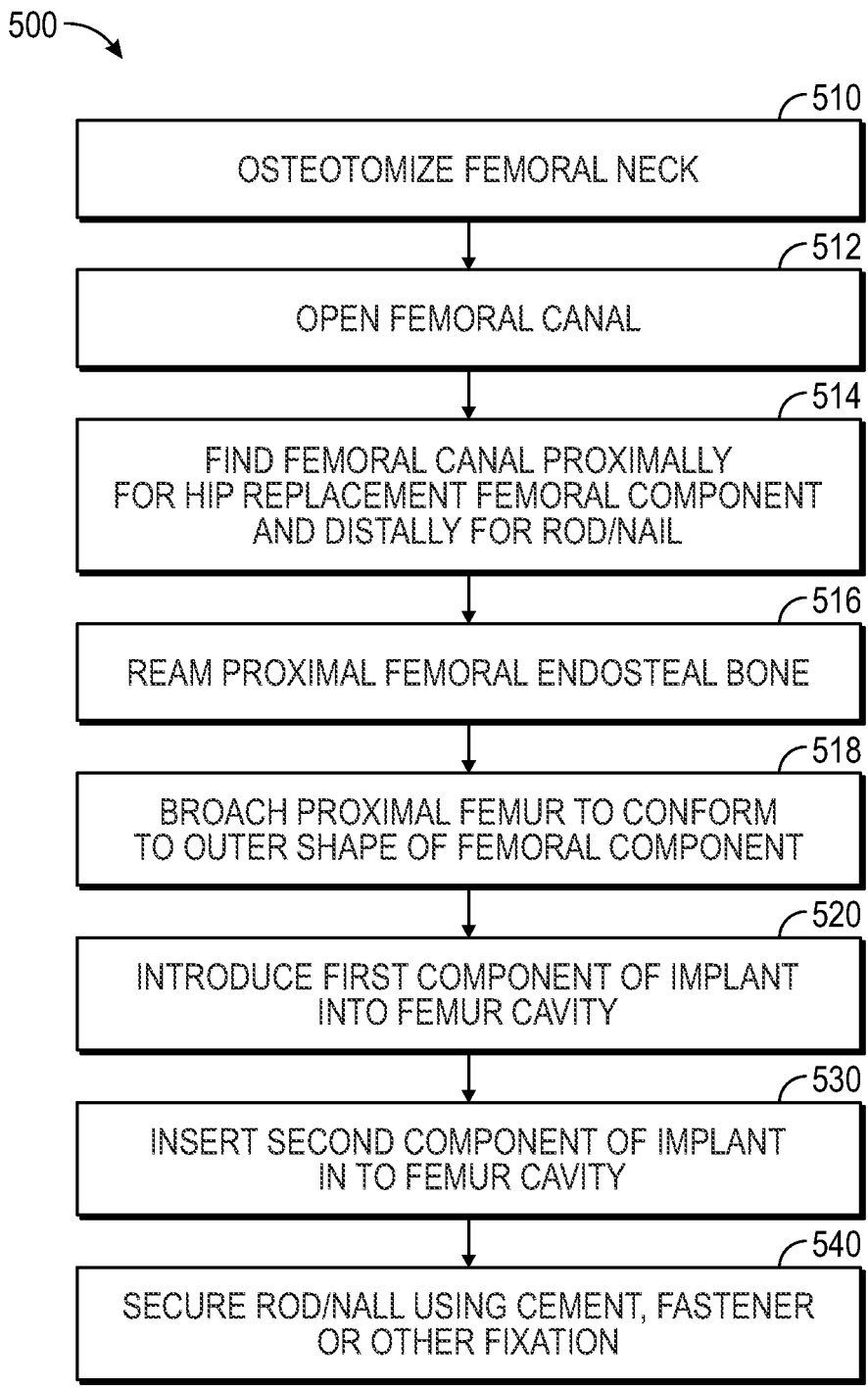
FIG. 5 is a flow diagram of an illustrative treatment procedure for securing an implant according to FIGS. 3 and 4 into a patient's femur.

Reference is made to the flow diagram of FIG. 5, which shows a treatment procedure for implanting a hip replacement implant 300 of FIGS. 3 and 4 within a cavity formed in a patient's femur, according to an illustrative embodiment. This procedure 500 can generally employ a system of conventional hip instruments, which are used to perform the following actions:

A. Conventional Hip Replacement Procedural Steps:

The practitioner first osteotomizes the patient's femoral neck (step 510), and opens the femoral canal (step 512). Then, the practitioner finds the femoral canal proximally for femoral component 310, and distally for the intramedullary rod/nail 320) in step 514. Once found, the practitioner then reams the proximal femoral endosteal bone (step 516), and broaches the proximal femur to conform to a femoral prosthesis shape (step 518).

B. Implant-Specific Procedural Steps:

At this point, the first component of the implant 300 is introduced into the femur cavity (step 520). In an illustrative embodiment, this initial insertion would be the femoral component 310. The component would be cemented contemporaneously with insertion or otherwise press fit—in accordance with the associated securing technology employed. Once the femoral component is cemented/secured in place, the intramedullary rod/nail portion 320 of the implant would be measured and then driven into place using a mallet (step 530). The nail can be cemented or non-cemented and can include associated fixations—such as the above-described transverse screw(s) 410, 420 (step 540). As described above, in an alternate procedure, the first component inserted can be the rod/nail and the second component inserted can be an appropriately adapted femoral component.

IV. Conclusion

It should be clear that the above-described implant and associated procedure provides an improved arrangement for treating patients with weakened bone structures sue to degenerative diseases. This implant can also be employed in otherwise healthy patients as appropriate. The implantation technique is straightforward and follows most of the already conventional steps used in hip-replacement treatments.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. An implant for use in hip replacement comprising:
   a femoral component comprising a longitudinal fenestration including an upper cranial region that is disposed atop an intermediary tapered interconnection region, and a distal elongated region that is disposed below the intermediary tapered interconnection region; and
   a securing, intermedullary rod constructed of three continuous regions, the three continuous regions comprising:
   an upper region having a diameter shaped and sized to define a close engagement with the femoral component at the upper cranial region,
   an intermediary tapered region received by the femoral component in a locking arrangement through engagement at the intermediary tapered interconnection region, and
   a distal region that engages with the distal elongated region.

2. The implant as set forth in claim 1 wherein the femoral component defines a shaft adapted to seat within a cavity formed in a proximal end of a patient's femur.

3. The implant as set forth in claim 2 wherein the rod includes at least one securing fastener at a distal end thereof.

4. The implant as set forth in claim 2 wherein the femoral component includes an arm that carries a ball joint.

5. The implant as set forth in claim 2 wherein at least one of the femoral component and the rod are arranged to be cemented into the cavity.

6. A method for hip replacement comprising the steps of:
   (a) preparing a proximal end of a patient's femur to define a cavity for receiving an implant having a ball joint;
   (b) inserting, into the cavity, a first component of the implant; and
   (c) inserting a second component into the cavity in engagement with the first component proximate to the proximal end at an upper region shaped and sized to define a close engagement therebetween, at a distal region, and at an intermediary tapered interconnection region disposed between the upper region and the distal region to define a locking relationship.

7. The method as set forth in claim 6 wherein the first component is a femoral component having the ball joint and a shaft with a fenestration, and the second component is an intermedullary rod that engages the fenestration in a locking relationship.

8. The method as set forth in claim 7 wherein the fenestration and a proximal end of the rod each define engaging tapered segments that are sized and arranged to interengage in the locking relationship.

9. The method as set forth in claim 6 wherein the first component is an intermedullary rod, and the second component is a femoral component having the ball joint and a shaft with a fenestration, wherein a proximal end of the rod engages the fenestration.

10. The method as set forth in claim 6 wherein either the first component or the second component is an intermedullary rod, and further comprising the step of securing the intermedullary rod into the cavity with at least one of fastener(s) and cement.

11. The implant as set forth in claim 1, wherein the cranial region is sized to define a close engagement with the upper region of the intermedullary rod and the distal elongated region is narrower than the cranial region and sized to closely conform to a portion of the distal region of the intermedullary rod.

12. The implant as set forth in claim 1, wherein the cranial region and the distal elongated region are each substantially uniform in diameter.

13. The method as set forth in claim 6 wherein the upper region and the distal region are each distinctly uniform in diameter.

14. An implant for use in hip replacement comprising:
- a femoral component comprising a ball joint receiving end, and an elongated shaft extending from the ball joint receiving end and configured for insertion into a femur of a patient, the elongated shaft including a longitudinal fenestration comprising an upper cranial region disposed above an intermediary tapered interconnection region, and a distal region disposed below the intermediary tapered interconnection region; and
- a securing, intermedullary rod comprising a femur-proximal portion shaped to engage with the femoral component at each of the upper cranial region, the intermediary tapered interconnection region, and the distal region, the rod further comprising a femur-distal portion configured to pass through the longitudinal fenestration, wherein the intermedullary rod is received by the femoral component in a locking arrangement through engagement of the intermediary tapered interconnection region of the longitudinal fenestration with a corresponding intermediary tapered region of the intermedullary rod.

* * * * *